(12) United States Patent
Hull, Jr.

(10) Patent No.: US 6,773,422 B2
(45) Date of Patent: Aug. 10, 2004

(54) FOLDED COMPACT TAMPON APPLICATOR

(75) Inventor: Raymond J. Hull, Jr., Hampton, NJ (US)

(73) Assignee: McNeil-PPC, Inc., Skillman, NJ (US)

(*) Notice: Subject to any disclaimer, the term of this patent is extended or adjusted under 35 U.S.C. 154(b) by 0 days.

(21) Appl. No.: 09/815,139

(22) Filed: Mar. 22, 2001

(65) Prior Publication Data

US 2002/0138035 A1 Sep. 26, 2002

(51) Int. Cl.$^7$ ................................................ A61F 13/20
(52) U.S. Cl. ............................ 604/385.17; 604/355.18
(58) Field of Search .............................. 604/11–18, 57, 604/59, 60, 288, 385.17, 385.18

(56) References Cited

U.S. PATENT DOCUMENTS

| | | | | |
|---|---|---|---|---|
| 2,222,088 A | * | 11/1940 | Peterson | 604/17 |
| 2,330,257 A | | 9/1943 | Bailey | |
| 2,351,836 A | | 6/1944 | Popper | |
| 2,518,486 A | * | 8/1950 | Mende | 604/11 |
| 3,831,605 A | * | 8/1974 | Fournier | 604/17 |
| 4,269,187 A | * | 5/1981 | Sakurai et al. | 604/17 |
| 4,273,125 A | | 6/1981 | Sakurai | |
| 4,291,696 A | | 9/1981 | Ring | |
| 4,508,531 A | | 4/1985 | Whitehead | |
| 4,557,720 A | | 12/1985 | Hemphill | |
| 4,755,164 A | | 7/1988 | Hinzmann | |
| 5,346,468 A | | 9/1994 | Campion et al. | |
| 5,350,371 A | | 9/1994 | Van Iten | |
| 5,782,793 A | | 7/1998 | Nielsen et al. | |
| 5,827,214 A | | 10/1998 | Fox et al. | |
| 5,910,520 A | | 6/1999 | Dabi et al. | |
| 6,171,426 B1 | | 1/2001 | Blanchard | |
| 6,186,973 B1 | | 2/2001 | Buzot | |
| 6,217,542 B1 | * | 4/2001 | Stevens et al. | 604/17 |
| 6,248,089 B1 | * | 6/2001 | Porat | 604/17 |

FOREIGN PATENT DOCUMENTS

| | | |
|---|---|---|
| DE | 19 48 979 A | 4/1971 |
| EP | 0616797 A1 | 9/1994 |
| GB | 744 209 A | 2/1956 |
| GB | 2 204 495 A | 11/1988 |
| GB | 2204495 A * | 11/1988 |
| WO | WO 99/33429 | 7/1999 |

OTHER PUBLICATIONS

PCT International Search Report, dated Oct. 8, 2002, for PCT Appln. No. PCT/US02/09028.
U.S. patent application Ser. No. 09/454,989.

* cited by examiner

Primary Examiner—John J. Calvert
Assistant Examiner—Jacqueline F Stephens

(57) ABSTRACT

An applicator system for delivering an object into mammalian body cavity and a method for delivering the object are disclosed. The applicator includes a tubular insertion member having a perimeter and an expulsion member, which is slideably fitted within the insertion member and linearly-biased. The expulsion member extends out of the gripper end of the insertion member and is restrained proximate the outer surface of the insertion member. The perimeter of the folded applicator about both the insertion and expulsion members is of similar length to that of the insertion member. The method includes the steps of releasing the expulsion member from restraint such that it extends rearwardly from the insertion member, inserting the insertion member into the body cavity, applying force on the expulsion member, expelling the object into the body cavity, and removing the insertion portion of the applicator.

19 Claims, 5 Drawing Sheets

US 6,773,422 B2

FOLDED COMPACT TAMPON APPLICATOR

FIELD OF THE INVENTION

The present invention relates to applicator systems for delivering materials into mammalian body cavities having a compact format in which the expulsion member is manipulated to present a shorter than normal length during storage. The applicator is particularly useful for delivering intravaginal devices, such as catamenial devices, into a vaginal canal.

BACKGROUND OF THE INVENTION

Applicators for delivering materials into a body cavity typically comprise a tubular insertion member having an insertion end and a gripper end opposite thereof, and an elongate expulsion member slideably fitted within the tubular insertion member for expelling the contained materials. A class of applicators is known as compact applicators, because they present a shorter packaged size, especially length, than required for use.

One type of compact applicator has an insertion member adapted to contain the insertable device and an expulsion member that is stored between the insertable device and the insertion member, e.g., in an annular space between a cylindrical tampon and a cylindrical, tubular insertion member. An example of this type of compact applicator is shown in Ring, U.S. Pat. No. 4,291,696. This type requires the user to prepare the applicator for use by first partially withdrawing the expulsion member in a controlled manner prior to pushing against the insertable device to expel it from the insertion member. This step introduces significant complexity to the applicator, as the insertable device must be prevented from following the expulsion member as it is withdrawn. Additionally, the expulsion member should also be somehow prevented from being completely removed from the insertion member.

A second type of compact applicator stores substantial portions, if not all, of the expulsion member outside of the insertion member. One example of this approach is disclosed in Buzot, U.S. Pat. No. 6,186,973B1. This applicator includes an external pusher element that is bent and inserted through an opening in the applicator to bear on a rear surface of the tampon. While this is an interesting and promising advance in the art, it requires several manipulations by the user prior to expelling the tampon from the applicator.

Another approach is described in Sakurai et al. U.S. Pat. No. 4,269,187. This approach incorporates a push-out top end contained within an outer cylinder and at least one inserting supporting piece connected to the push-out top end and folded outwardly from the outer cylinder. A preferred embodiment of this device incorporates a pair of such outwardly folded elements supporting pieces that are locked together prior to use. Again, this approach also appears to require the user to actively unfold and manipulate the push-out elements prior to use.

Therefore, what is needed is a compact applicator that requires little manipulation by a user prior to use and that is robust to reliably and easily expels an insertable object contained therein.

SUMMARY OF THE INVENTION

An applicator system for delivering an object into a mammalian body cavity is disclosed. The applicator includes a tubular insertion member arranged and configured to contain the object and a linearly-biased expulsion member having a first end slideably fitted within the tubular insertion member. The tubular insertion member has an insertion end and a gripper end, opposite thereof. The expulsion member extends out of the gripper end of the tubular insertion member, and terminates in a second end. The applicator also includes an expulsion member restraint capable of restraining the second end of the expulsion member proximate an outer surface of the insertion end of the tubular insertion. The expulsion member is bent when so restrained.

The invention also relates to a method of delivering an object into a body cavity from an applicator. In this method, the applicator is substantially as described above, and the method includes the steps of: a) releasing the expulsion member restraint to permit the expulsion member to spontaneously attain a substantially linear configuration with the second end extending rearwardly away from the gripper end of the tubular insertion member; b) inserting the insertion end of the tubular insertion member into the body cavity; c) applying force on the second end of the expulsion member to move the first end thereof toward the insertion end of the tubular insertion member; d) expelling the object out of the insertion end of the tubular insertion member and into the body cavity; and e) removing the applicator from the body cavity.

DETAILED DESCRIPTION OF THE INVENTION

As used in herein the specification and the claims, an element is "linearly-biased" if it tends to exhibit a substantially linear configuration in the absence of significant outside forces. For example, an element that is capable of being bent under an outside influence, such as a restraint, and of spontaneously reverting to a substantially linear configuration when the outside influence is removed is a linearly-biased element.

The term "diameter" as used in herein the specification and the claims relates to a chord passing through the center of a figure or body, and it can be measured as the length of this straight line (chord) through the center of the body in a given plane. Unless otherwise noted, this plane is perpendicular to the major longitudinal axis of the body. In a non-circular cross-section, the body may have a maximum diameter and a minimum diameter.

As used herein, a "unitary" device is one that has the characteristic of being a unit or a whole. This includes both devices that are created from a single element and those formed by fixing together individual elements to form the whole.

As used herein the specification and the claims, the term "intravaginal device" and related terms includes support devices, obstructing devices useful to block the flow of and/or collect bodily liquids, and the like. The term includes, without limitation, incontinence devices and vaginal supports, such as pessaries; and obstructing devices, such as menstrual collection cups and inflatable or expandable vaginal blocking devices (devices which do not, themselves, absorb the bodily liquids).

While the present invention generally relates to applicator devices having a tubular insertion member, the following detailed description will refer, specifically, to a tampon applicator for ease of understanding. One of ordinary skill in the art will recognize other uses for this invention.

Figure 1:
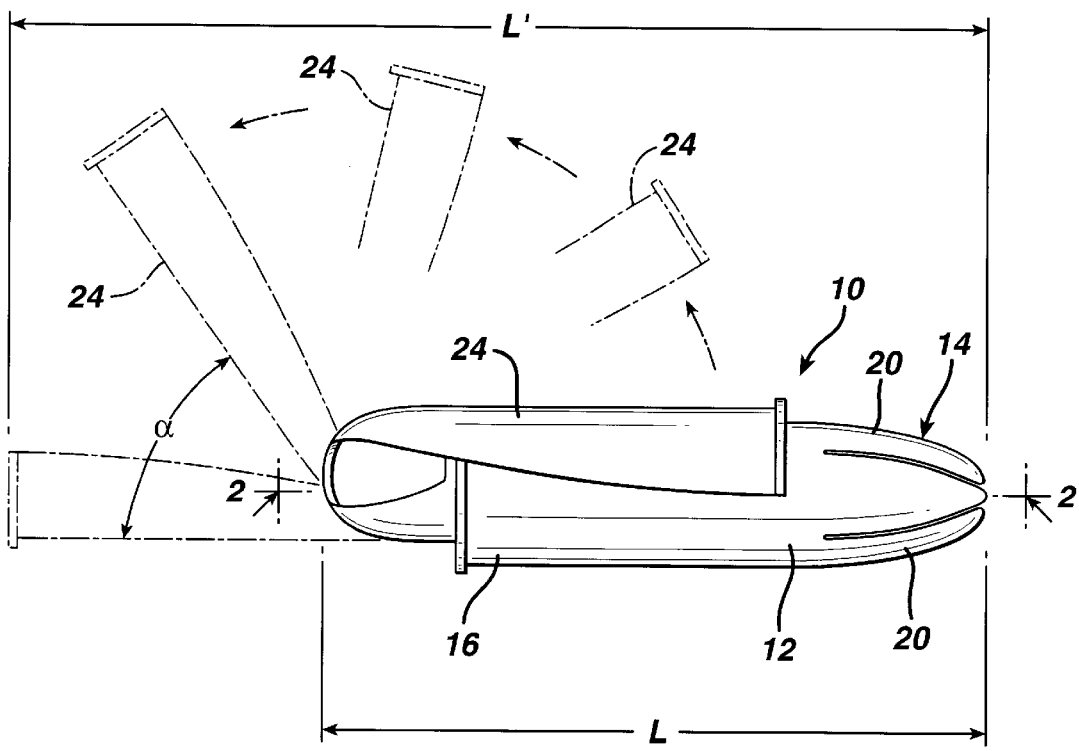
FIG. 1 is a side elevation of a compact tampon applicator according to the present invention in its stored or packaged configuration and, in phantom, locations of a portion of the expulsion member as it moves into a ready-for-use configuration.
Figure 2:
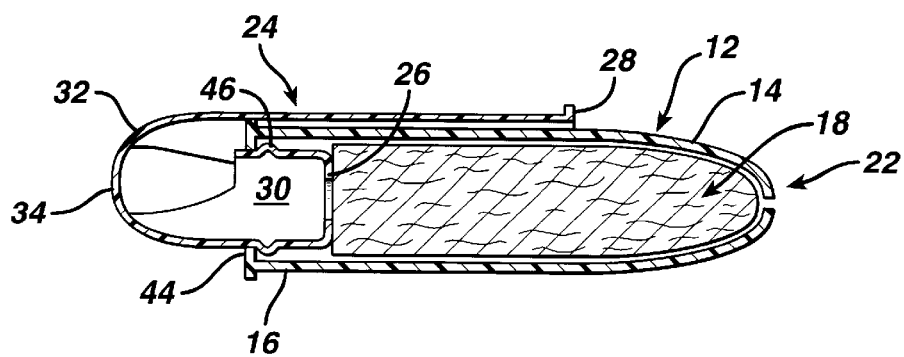
FIG. 2 is a cross-section of the side elevation of FIG. 1.

Referring now to the drawings, wherein like reference numerals designate like elements, FIGS. 1 and 2 depict an applicator 10, comprising a tubular insertion member 12, having an insertion end 14 and a gripper end 16 that is suitable to contain a tampon 18 that can be delivered into the body cavity. The insertion end may have a plurality of inwardly curved petals 20 that form a substantially closed feature 22. The applicator 10 also includes a linearly-biased expulsion member 24 having a first end 26 that is insertable into the tubular insertion member 12 and is capable of bearing against the tampon 18. The expulsion member 24 terminates in a second end 28, opposite the first end 26, that may be manipulated to move the first end 26 within the tubular insertion member 12. The first end 26 of the expulsion member 24 is arranged and configured to be slideably introduced into the tubular insertion member 12 through its gripper end 16.

The applicators 10 or other tubular devices of the present invention can have tube geometries or cross-sections that are useful to contain the object to be inserted. Often, the shape of the tampon 18 or other element contained suggests the shape of the tubular insertion member 12, but departures from this general rule may be made. Therefore, the tubular insertion member 12 may take on numerous cross-sectional shapes including, without limitation, circular, oval, polygonal (e.g., trapezoidal, rectangular, triangular), and the like. For example, cylindrical tampons may be contained within rectangular insertion members and trapezoidal tampons (such as those disclosed in Van Iten et al., U.S. Pat. No. 5,350,371) and cup-shaped tampons (such as those disclosed in Bailey, U.S. Pat. No. 2,330,257) can be contained in a generally cylindrical insertion member. In addition, the insertion member 12 can substantially elongated, curved, or flexible, or it can take on other shapes that are apparent to one of ordinary skill in the art. The specific geometry, itself, is not critical to the practice of the present invention. In addition, the edge of the tubular device (both finished and unfinished) may be a standard, planar edge coincident with a plane perpendicular to the longitudinal axis of the tubular device. However, the edge may also be coincident with a plane oblique to the longitudinal axis, or it may be otherwise contoured and/or recessed as described in the commonly assigned, copending application of Buzot, U.S. Ser. No. 09/454,989 now U.S. Pat. No. 6,533,748 (herein incorporated by reference).

The first end 26 of the linearly-biased expulsion member 24 is provided to bear against the rear end 19 of the tampon 18, especially as it is use to expel the tampon 18. In order to expel the tampon 18 effectively, it is useful to provide a first portion 30 of the expulsion member 24 located adjacent the first end 26. It is preferred that the first portion 30 has a length that is sufficient to provide some directional stability to the expulsion member 24 in the tubular insertion member 12. In particular, it is preferred that the enlarged portion 30 corresponds to the size and shape of the interior of the gripper end 16 of the tubular insertion member 12 proximate the first portion 30. This allows the expulsion member 24 to more easily slide within the tubular insertion member 12 without binding or becoming jammed.

Figure 3:
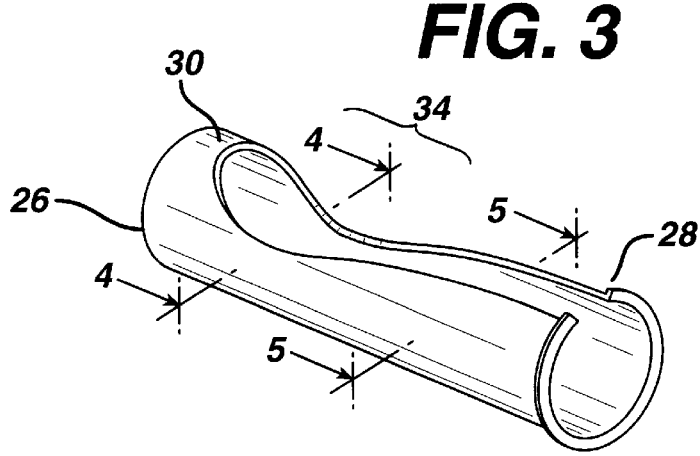
FIG. 3 is a perspective view of an expulsion member useful in the present invention.

The expulsion member 24 (shown alone in FIG. 3) also has a second portion 32 extending from the first portion 30 to the second end 28. Preferably, the second portion is formed of a beam 32 having a reduced cross-section in comparison to the first portion 30. As this beam 32 is used to transmit force exerted on the second end 28 along the expulsion member 24 and through the first portion 30 to the tampon 18, the second portion should have sufficient column strength and rigidity to transmit such linear forces without significant deformation. While the linear forces encountered in use of applicators may vary, it is preferred that the beam 32 be capable of withstanding a linear force sufficient to expel the tampon 18 into a user's vaginal canal without buckling. Generally, this force is at least about 5 N (Newtons), more preferably, at least about 10 N, and most preferably, at least about 15 N. This column strength can be determined by securing the first portion of the expulsion member into an appropriately sized receptacle placed on the fixed jaw of a Instron Universal Testing Machine, available from Instron Corporation, Canton, Mass., USA, to prevent the first portion from twisting or bending. The moveable jaw is brought to contact the second end of the expulsion member and is then set to compress the expulsion member at a rate of about 5 cm/minute. The force exerted on the expulsion member is measured continuously, and the point at which this force begins to fall instead of rise is the point at which the expulsion member buckles. The maximum force achieved is the column strength of the expulsion member. Notwithstanding the required column strength and rigidity necessary to transmit the expulsion forces, the beam must also be sufficiently flexible to be bent into a compact configuration, again without permanent damage to itself, such as a permanently set bent configuration.

The proportion of the expulsion member 24 provided by the first portion 30 and by the second portion 32 can vary. However, the first portion 30 preferably has sufficient length and other external dimensions to help it to be predictably oriented in the tubular insertion member 12. For example, it is helpful if the first portion has dimensions to allow it to slide within the tubular insertion member 12 while maintaining a substantially uniform orientation to the longitudinal axis of the insertion member 12. These dimensions may include a length that is approximately equal to the maximum diameter of the first portion 30 or greater.

The second portion 32 preferably has sufficient length to be wrapped back towards the insertion end of the tubular insertion member 12. Thus, it preferably extends about ¾ of the length of the expulsion member or less. This provides a sufficient length to dispense an object from the tubular insertion member 12. An additional relationship can be the relationship of the packaged length of the applicator 10 having a bent expulsion member 24. Thus, it is preferred that the packaged length of the applicator ("L" as shown in FIG. 1) is less than about 70% of the length of the applicator 10 having an extended expulsion member 24 ("L'" as shown in FIG. 1), and more preferably, less than about 60%.

The second portion 32 is preferably a beam, and it can have any cross-section that effectively transmits the linear forces described above and permits the required bending. A representative, non-limiting list of useful cross-sections include circular, oval, and the like; polygonal including triangular, trapezoidal, parallelograms such as rectangular, rhomboidal, and the like; "I"-section; angle sections; "T"-sections; "Z"-sections; "H"-sections; channel-section, including standard channel-sections with substantially straight base and walls, "U"-sections, and sections defined by circular segments; and other sections that provide the appropriate balance of column strength and rigidity under linear forces aligned with the longitudinal axis of the beam and flexibility under forces directed at an angle to the longitudinal axis of the beam. Preferred cross-sections of the beam include channel sections, and especially preferred cross-sections include channel-sections defined by circular segments. Such circular segments may be further described by their central angle, $\theta$.

In a preferred embodiment, the first portion is an enlarged portion, and the second portion comprises a beam having a reduced cross-sectional area in comparison to the enlarged portion. This provides a good bearing surface against the tampon, corresponds to the larger interior dimensions of the tubular insertion member, and allows a less bulky beam to extend outwardly from the tubular insertion member that can be bent around the insertion member for more discrete packaging.

Preferably, expulsion member 24 has a hinge portion 34 intermediate the first end 26 and the second end 28. In a particularly preferred embodiment, the hinge portion 34 is adjacent the enlarged portion 30 of the expulsion member 24. The hinge portion 34 provides a defined bending location for the expulsion member 24. However, unlike unbiased hinges, the hinge portion 34 doesn't affect the linear bias of the expulsion member 24. Therefore, the hinge portion 34, in addition to the usual characteristic of providing a bending location, must be able to transmit linear force from the second end 28 of the expulsion member 24 to the first end 26 and to provide a mechanism to return the expulsion member 24 to a substantially linear configuration once an outside, bending influence is removed.

Useful hinge portions 34 can be provided by an unmodified portion of the beam 32; by a modified portion of the beam 32; by an added, biased hinge element such as a spring-biased hinge; and by any other useful element that provides the properties and characteristics described above.

Figure 4:
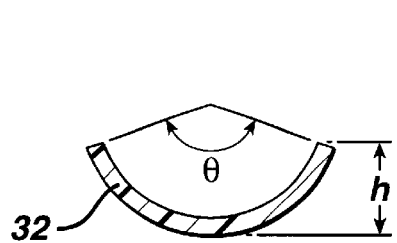
FIGS. 4 and 5 are cross-sections taken along lines 4—4 and 5—5 of FIG. 3.
Figure 5:
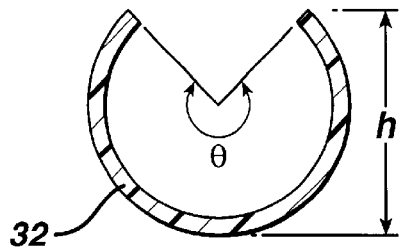
Figure 6A:
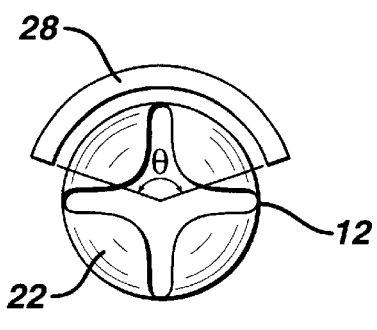
FIGS. 6A and 6B are end elevations of two embodiments of applicators according to the present invention.
Figure 6B:
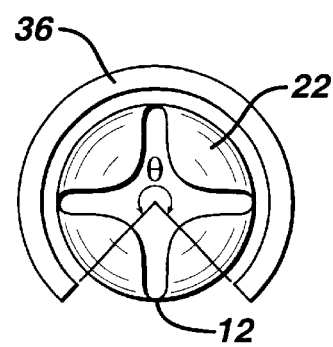

Preferably, the hinge portion 34 is provided by an unmodified portion of the beam 32, if the beam 32 is sufficiently flexible to bending moments (or forces) by itself, or by a modified portion of the beam 32, such as a localized reduction in wall height of a channel-section beam. As used herein the specification and the claims, the term "wall height" relates to a measure of the distance from the uppermost edges of a channel wall or the ends of a circular segment down to the base of a substantially flat-bottomed channel or the midpoint of the circular segment. These measurements can be seen in FIGS. 4 and 5. Other modifications of beam sections can be used. For example, one or more flanges may be locally reduced or removed from a hinge portion of "I"-, "H"-, "Z"-, "T"-, or angle section beams. In the case of the hinge portion 34 formed of either a modified or unmodified portion of the beam 32, it is preferred that the hinge portion 34 provides a gradual bend of the beam in contrast to a localized angle or crease. This gradual bend results in significantly less material damage of the beam 32 and provides more spring-back upon release.

Preferably, the hinge portion 34 provides sufficient spring-back to provide an angle $\alpha$ upon release of less than 90°, more preferably, less than about 60°, and most preferably, about 0°. As can be seen in FIG. 1, this angle $\alpha$ is the amount by which the spring-back of the material fails to provide a straight beam 32. This provides a more rigid structure to transmit the expulsion force applied to the second end 28 through the expulsion member 24 to the tampon 18.

The applicator 10 also includes an expulsion member restraint capable of restraining the second end 28 of the expulsion member 24 proximate an outer surface of the insertion end 14 of the tubular insertion member 12 such that the expulsion member 24 is bent when so restrained. The restraint may be unitary with the applicator, or it may be external to the applicator. Unitary restraints can be unitary with the tubular insertion member 12 or, preferably, unitary with the expulsion member 24. In several embodiments, illustrated in FIGS. 1–3 and 6–11, the restraint is unitary with the second end 28 of the expulsion member 24. The first of these embodiments, shown in FIGS. 1–3 and 6A and 6B, the expulsion member 24 has a tubular enlarged portion 30 and a beam 32 having a cross-section substantially corresponding to a circular segment having a first central angle providing a first wall height. The second end 28 has a unitary mechanical catch 36 in the form of a portion of the beam having a larger central angle, greater than about 180° providing a greater wall height. The increased central angle provides a mechanical catch 36 that is capable of engaging an outer surface of the tubular insertion member 12, especially when the tubular insertion member 12 is cylindrical.

Figure 7:
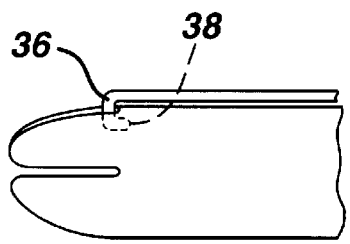
FIG. 7 is a detail of the insertion end of a tubular insertion member and the second end of an expulsion member according to an alternative embodiment of the present invention.

Another embodiment in which the restraint is a mechanical catch that is unitary with the second end 28 of the expulsion member 24 is shown in FIG. 7. In this embodiment, the mechanical catch 36' is a hook 38. This hook 38 is oriented to engage with a gap disposed between adjacent petals 20 at the insertion end 14 of the tubular insertion member 12. The hook 38 is sufficiently flexible to be released from this gap to allow the expulsion member 24 to reacquire its substantially linear orientation.

Figure 8:
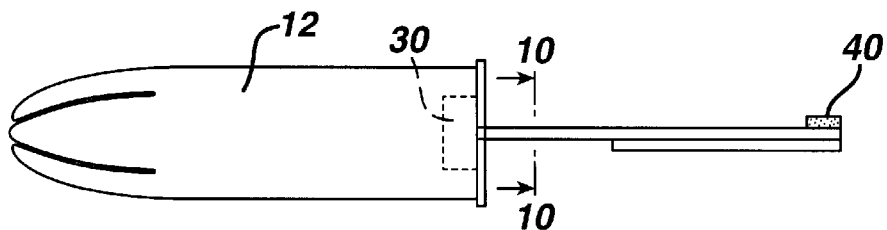
FIG. 8 is a side elevation of an alternative embodiment of the present invention in a ready-for-use configuration.
Figure 9:
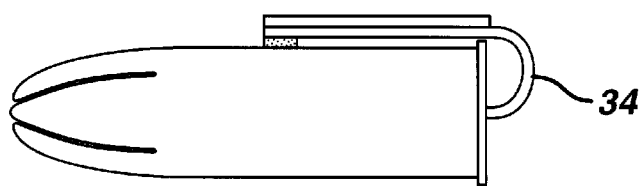
FIG. 9 is a side elevation of the alternative embodiment of FIG. 8 in a stored or packaged configuration.
Figure 10:
FIG. 10 is a cross-section of the hinge portion of the beam in the alternative embodiment of FIG. 8, taken along line 10—10.

Yet another restraint that is unitary with the expulsion member 24 is based upon an adhesive material 40 disposed on the second end 28 of the expulsion member 24. An example of this embodiment is shown in FIGS. 8–10, which also illustrate a "T" cross-section beam 32. Preferably, the adhesive material 40 is a pressure sensitive adhesive that is substantially non-transferable to the outer surface of the tubular insertion member 12.

Figure 11:
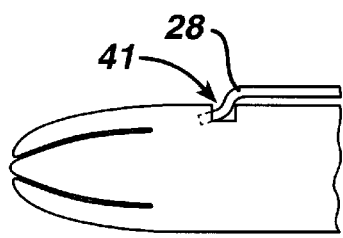
FIG. 11 is a detail of the insertion end of a tubular insertion member and the second end of an expulsion member according to an alternative embodiment of the present invention.

In addition, the restraint may be unitary with the tubular insertion member 12. An example of such a restraint is shown in FIG. 11 in which the tubular insertion member 12 has an aperture 41 or a receptacle (not shown) provided therein to accept at least a portion of the second end 28 of the expulsion member 24.

Figure 12:
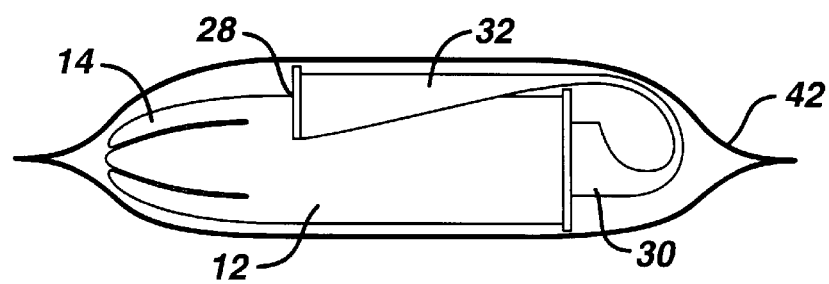
FIG. 12 is a side elevation of an alternative embodiment of the present invention in a packaged configuration.
Figure 13:
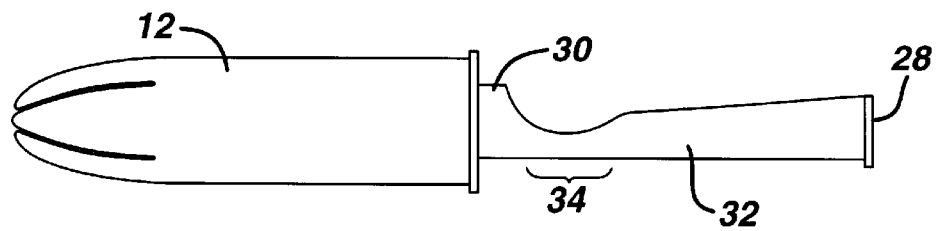
FIG. 13 is a side elevation of the alternative embodiment of FIG. 12 in an unpackaged, ready-for-use configuration.

Alternatively, the restraint may be external to the applicator as shown in FIGS. 12 and 13. Preferably, the external restraint substantially surrounds the expulsion member second end 28 and the tubular insertion member 12. In a particularly preferred embodiment, the external restraint is formed of packaging material 42. Of course alternatives may be employed, such as a band of elastic material, plastic, or even paper.

Additional features may be incorporated into the tubular insertion member 12 and/or expulsion member 24. For example, one or both members may incorporate features to help keep them together prior to and during use. The tubular insertion member 12 may incorporate an internally directed stop 44 to help to contain the tampon 18 and the first portion 30 of the expulsion member 24. In addition, the expulsion member 24 may incorporate one or more raised features, such as a raised ring 46. This raised feature 46 can interact with the internally directed stop 44 to improve the ability of the tubular insertion member 12 and the expulsion member 24 to remain interlocked. The expulsion member 24 may also incorporate a locking device to reinforce the hinge portion 34 to prevent premature collapse or otherwise increase the column strength of the extended expulsion member 24.

The applicator devices of the present invention can be made of materials known to those of ordinary skill in the art. Generally, the tubular insertion members are plastic or paper. Plastic materials include, without limitation, polyolefins such as polyethylene and polypropylene (including polyolefin copolymers); polyesters such as polyethylene terephthalate; polyamides such as nylon; polyurethanes; polystyrene; polycaprolactone; polyvinyl alcohol; ethylene-vinyl acetate copolymers; elastomers such as silicones, natural rubbers, and synthetic rubbers including block copolymers; cellophane; PHBV such as those disclosed in Dabi et al., U.S. Pat. No. 5,910,520 (herein incorporated by reference); starch-based polymers including those disclosed in Dabi et al., U.S. Pat. No. 5,910,520; and the like.

Paper materials include, without limitation, paperboard, cardboard, cup stock, paper, and the like. The paper may be a single layer of material, or it can be a plurality of laminated layers to provide multiple benefits relating to the various layers. Laminated paper material may include a surface layer or coating of plastic, wax, silicone, lubricants, and the like, which may be useful to increase the comfort to the user during insertion and withdrawal. The plastic coating may include, without limitation, those plastic materials listed above. Laminated paper material may also include additional layers such as adhesive layers, tie layers, and the like.

An example of such a surface layer is disclosed in Blanchard, U.S. Pat. No. 6,171,426. A representative, non-limiting list of useful materials to be used as the surface layer includes, waxes, cellophane, polyolefins, polyesters, epoxies, and the like. The surface layers may also include thermal stabilizers, pigments, fragrances, surfactants, antimicrobial agents, medicaments, and the like.

The tubular insertion member 12 of the applicator 10 provided by the present invention is preferably substantially closed prior to expulsion of the materials contained therein. Alternatively, the insertion end of the applicator can be more or less open, that is the diameter along the length of the tubular insertion member is substantially equivalent to the diameter of the insertion end. Procter & Gamble, of Cincinnati, Ohio, currently offers for sale an open-ended tampon applicator under the trade name TAMPAX flushable applicator tampons.

The expulsion member 24 of the applicator 10 provided by the present invention can be made from the same materials as discussed above for the tubular insertion member 12. However, although paper is not as useful unless modified substantially to provide the appropriate spring-back, and some metals such as superelastic metal alloys such as Nitinol (Ni—Ti alloy) may also be used. However, plastics are most preferred materials. The above, representative list of plastics useful for the tubular insertion member are also useful for the expulsion member. The expulsion member 24 having a modified hinge portion 34 may also be optimized by determining a minimum beam dimension for the hinge portion 34 to provide the appropriate column strength to resist buckling failure during expulsion. This minimum beam dimension may also reduce the likelihood that the beam would become irrecoverably damaged during the bending of the hinge portion 34 to allow the desired spring-back. Additionally, reinforcements to the remainder of the beam 32 may provide benefits in use. This may be especially true in providing appropriate column strength.

Typical dimensions for each of the tubular insertion and expulsion members include a length of from about 50 to about 100 millimeters, a diameter of from about 8 to about 16 millimeters, and a thickness of from about 0.4 to about 0.6 millimeters. Preferably, the diameter of the expulsion member is less than the diameter of the tubular insertion member to allow for a telescopic arrangement of the two.

The applicator of the present invention can be made by appropriate processes that will be recognized by those of ordinary skill in the art. For example, paper tubular insertion members can be constructed from a single layer of paper material, or from a plurality of laminated layers to provide multiple benefits relating to the various layers. The applicators can be made from sheets of material using several processing including, without limitation: spiral winding as disclosed in Campion et al., U.S. Pat. No. 5,346,468, convolute winding as disclosed in Whitehead, U.S. Pat. No. 4,508,531, and forming a sheet around a mandrel and then sealing an overlapped seam as disclosed in Hinzmann, U.S. Pat. No. 4,755,164.

If the applicator includes a surface layer, as described above, it may be applied using any useful technique. Many techniques are known for applying the surface layers. A representative, non-limiting list of such techniques includes spraying, extruding, slot-coating, brushing, transfer coating, and the like. Additional processing steps may be required to cure the surface treatments to a useable form other than simple air curing, such as applying irradiation or other forms of energy.

Again, the tubular insertion member of the applicator provided by the present invention is preferably substantially closed prior to expulsion of the materials contained therein. One technique for substantially closing the insertion end of the applicator is by employing a plurality of inwardly curved petals. The petals will flex and/or hinge to an open position upon expelling materials contained by the applicator. The number of petals generally ranges from about four to about six. An alternative technique for substantially closing the insertion end of an applicator is by pleating the insertion end. This technique is disclosed in Neilsen et al., U.S. Pat. No. 5,782,793. When an applicator is constructed with more than one layer of material, a single layer may extend into the insertion end in an effort to reduce the force required to expel the contained materials. An example of this is disclosed in Fox et al., U.S. Pat. No. 5,827,214. These collective closures may be of spherical shape, or alternatively tapered shape.

Plastic applicator members may be manufactured using any useful technique, and many techniques are known for manufacturing plastic applicators. A representative, non-limiting list of such techniques includes injection-molding, blow-molding, extrusion, formation from one or more sheets (as described above for paper), and the like. Generally, the applicator members (for example, the tubular insertion members) can be formed through an injection molding process. This process may be used, because it allows the manufacture to balance some key characteristics of the tubular insertion member. Mold inserts and cores can be machined to form a slightly tapered product. For example, the wall thickness around the gripper end 16 is relatively thick to maintain structural stability during the insertion and expulsion steps of use, while the thickness in the insertion end 14 can be minimized to provide flexibility and low expulsion force. Injection molding also enables the manufacture to make uniquely shaped tubular insertion members and expulsion members. As mentioned above, the less sophisticated and/or less expensive techniques, such as extrusion and blow molding can also be employed. For example, extruded tubes can be further manipulated to form additional features, such as raised or indented rings or other formations. They can also have portions removed to form the hinge portion of the expulsion member. Extruded plastic tubes provide further orientation of the polymer. This orientation may be useful to increase the spring-back and column strength of the expulsion member.

The applicator of the present invention can be used for the delivery of an object into a mammalian body cavity. Such objects may include suppositories, absorbent devices, and the like, and they may be delivered into body cavities including the mouth, nose, vagina, urethra, and rectum. These materials may be in the form of solids, creams, foams, gels, and the like.

Preferably, the applicator is used to deliver intravaginal devices, including catamenial devices, such as tampons, intravaginal collection devices, and interlabial pads; birth control devices such as diaphragms or intrauterine devices (IUDs); compositions in the form of suppositories, such as medicaments, moisturizers, vitamins and minerals, spermicides, and odor controlling agents; medical devices and incontinence devices and vaginal supports such as pessaries; and obstructing devices. Obstructing devices include menstrual collection cups and inflatable or expandable blocking devices.

Figure 14:
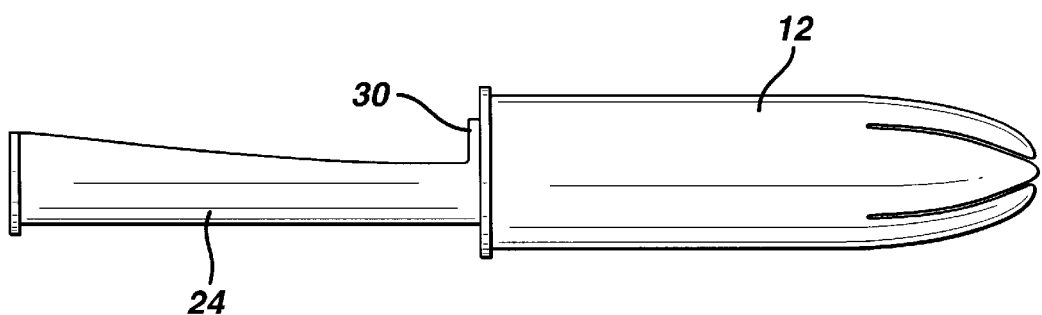
FIG. 14 is a side elevation of the embodiment of FIG. 1 in a ready-for-use configuration.
Figure 15:
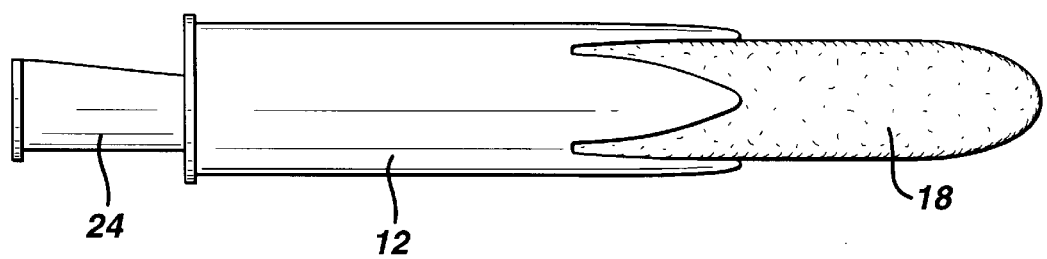
FIG. 15 is a side elevation of the embodiment of FIG. 1, as a contained tampon is being expelled.

In use, the applicator 10 can be removed from its packaging material, e.g., 42. If the packaging material 42 is used as an external restraint (as in FIG. 12), the expulsion member 24 would then automatically unfold to provide a substantially linear expulsion member 24, as shown in FIG. 13. Alternatively, the user may need to initiate separation of the second end 28 of the expulsion member 24 from the tubular insertion member 12 by releasing the mechanical catch 36 or adhesive material 40 to allow the expulsion member 24 to unfold (as shown in FIGS. 1 and 14). Next, a user may place insertion end 14 into the body cavity orifice, delivering tampon 18 into the body cavity by pushing on expulsion member 24 until tampon 18 is expelled from tubular insertion member 12 (as shown in FIG. 15) and withdrawing applicator 10 from the body, leaving tampon 18 within the body cavity.

Alternately, a user could pull tubular insertion member 12 onto expulsion member 24 while maintaining expulsion member 24 steady relative the user's body. This substantially eliminates friction between the tampon 18 and the user's body.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A tampon applicator comprising:
    a substantially cylindrical tubular insertion member having a longitudinal axis and a perimeter measured in a plane perpendicular to the longitudinal axis and arranged and configured to contain a tampon and having an insertion end and a gripper end opposite thereof;
    a linearly-biased expulsion member, a first end slideably fitted within the tubular insertion member, extending out of the gripper end of the tubular insertion member, and terminating in a second end and a hinge portion intermediate the first end and the second end;
    an expulsion member restraint comprising a mechanical catch that is unitary with the second end and has a cross-section corresponding to a circular segment with a central angle of greater than about 180° that is capable of engaging an outer surface of the substantially cylindrical tubular insertion member proximate the insertion end thereof such that when the expulsion member is bent and restrained, a perimeter of the resulting folded applicator measured in the plane perpendicular to the longitudinal axis and about both the tubular insertion member and the constrained expulsion member is similar to the perimeter of the insertion member.

2. The applicator of claim 1 wherein the expulsion member comprises an first portion proximate the first end and a channel-section beam extending toward the second end.

3. The applicator of claim 2 wherein the channel-section beam extends about 75% of the length of the expulsion member or less.

4. The applicator of claim 3 wherein the channel-section beam comprises a hinge portion proximate the first portion.

5. The applicator of claim 4 wherein the hinge portion comprises a portion of the channel-section beam having a first wall height that is less than a second wall height of the channel-section beam proximate the second end.

6. The applicator of claim 4 wherein the hinge portion comprises a portion of the channel-section beam having a first thickness that is less than a second thickness of the channel-section beam proximate the second end.

7. The applicator of claim 1, wherein the expulsion member has sufficient rigidity to transmit linear forces without significant linear deformation when delivering the tampon from the tubular insertion member.

8. A method of delivering an object into a body cavity from an applicator, said applicator including a tubular insertion member arranged and configured to contain the object and having an insertion end and a gripper end opposite thereof, and a linearly-biased expulsion member having a first end slideably fitted within the tubular insertion member, extending out of the gripper end of the tubular insertion member, and terminating in a second end, and an expulsion member restraint which restrains the second end of the expulsion member proximate an outer surface of the insertion end of the tubular insertion member, the method comprising the steps of:

a) releasing the expulsion member restraint by disengaging an adhesively-attached portion of the expulsion member second end from the outer surface of the tubular insertion member to permit the expulsion member to spontaneously attain a substantially linear configuration with the second end extending rearwardly away from the gripper end of the tubular insertion member;

b) inserting the insertion end of the tubular insertion member into the body cavity;

c) applying a force differential between the expulsion member and the tubular insertion member sufficient to cause relative movement of the first end of the expulsion member toward the insertion end of the tubular insertion member;

d) expelling the object out of the insertion end of the tubular insertion member and into the body cavity; and e) removing the applicator from the body cavity.

9. An applicator for delivering an object into a mammalian body cavity comprising:

a) a tubular insertion member arranged and configured to contain the object and having an insertion end and a gripper end opposite thereof;

b) a linearly-biased expulsion member having a first end slideably fitted within the tubular insertion member, extending out of the gripper end of the tubular insertion member, and terminating in a second end; and c) an expulsion member restraint capable of restraining the second end of the expulsion member proximate an outer surface of the insertion end of the tubular insertion member such that the expulsion member is bent when so restrained;

wherein the expulsion member comprising (i) an enlarged portion proximate the first end and (ii) a channel-section beam, having a reduced cross-sectional area in comparison to the enlarged portion, extending toward the second end and having.

10. The applicator of claim 9 wherein the beam comprises a hinge portion having a first wall height that is less than a second wall height of the channel-section at the second end of the expulsion member wherein the hinge portion is adjacent the enlarged portion.

11. An applicator for delivering an object into a mammalian body cavity comprising:

a) a tubular insertion member arranged and configured to contain the object and having an insertion end and a gripper end opposite thereof;

b) a linearly-biased expulsion member having a first end slideably fitted within the tubular insertion member, extending out of the gripper end of the tubular insertion member, and terminating in a second end; and c) an expulsion member restraint capable of restraining the second end of the expulsion member proximate an outer surface of the insertion end of the tubular insertion member such that the expulsion member is bent when so restrained wherein the expulsion member restraint substantially surrounds the expulsion member second end and the tubular insertion member.

12. The applicator of claim 11 wherein the expulsion member restraint comprises packaging material and substantially encloses the applicator.

13. The applicator of claim 9 wherein the expulsion member restraint is unitary with the expulsion member second end.

14. The applicator of claim 13 wherein the expulsion member restraint comprises an adhesive material.

15. The applicator of claim 13 wherein the expulsion member restraint comprises a mechanical catch.

16. The applicator of claim 9 wherein the beam comprises a hinge portion having a first thickness that is less than a second thickness of the beam at the second end.

17. A method of delivering an object into a body cavity from an applicator, said applicator including a tubular insertion member arranged and configured to contain the object and having an insertion end and a gripper end opposite thereof, and a linearly-biased expulsion member having a first end slideably fitted within the tubular insertion member, extending out of the gripper end of the tubular insertion member, and terminating in a second end, and an expulsion member restraint which restrains the second end of the expulsion member proximate an outer surface of the insertion end of the tubular insertion member, the method comprising the steps of:

a) releasing the expulsion member restraint by removing an external element substantially surrounding the expulsion member second end and tubular insertion member to permit the expulsion member to spontaneously attain a substantially linear configuration with the second end extending rearwardly away from the gripper end of the tubular insertion member;

b) inserting the insertion end of the tubular insertion member into the body cavity;

c) applying a force differential between the expulsion member and the tubular insertion member sufficient to cause relative movement of the first end of the expulsion member toward the insertion end of the tubular insertion member;

d) expelling the object out of the insertion end of the tubular insertion member and into the body cavity; and e) removing the applicator from the body cavity.

18. The method of claim 17 wherein the step of releasing the expulsion member restraint comprises removing external packaging materials from around the applicator.

19. A method of delivering an object into a body cavity from an applicator, said applicator including a tubular insertion member arranged and configured to contain the object and having an insertion end and a gripper end opposite thereof, and a linearly-biased expulsion member having a first end slideably fitted within the tubular insertion member, extending out of the gripper end of the tubular insertion member, and terminating in a second end, and an expulsion member restraint which restrains the second end of the expulsion member proximate an outer surface of the insertion end of the tubular insertion member, the method comprising the steps of:

a) releasing the expulsion member restraint by disengaging a mechanical catch that is unitary with the expulsion member second end from the tubular insertion member to permit the expulsion member to spontaneously attain a substantially linear configuration with the second end extending rearwardly away from the gripper end of the tubular insertion member;

b) inserting the insertion end of the tubular insertion member into the body cavity;

c) applying a force differential between the expulsion member and the tubular insertion member sufficient to cause relative movement of the first end of the expulsion member toward the insertion end of the tubular insertion member;

d) expelling the object out of the insertion end of the tubular insertion member and into the body cavity; and e) removing the applicator from the body cavity;

wherein the tubular insertion member is substantially cylindrical and the step of releasing the expulsion member restraint comprises disengaging from the tubular insertion member a mechanical catch (1) that is unitary with the expulsion member second end and (2) that has a circular cross-section with a central angle of greater than about 180° and (3) fits around the tubular insertion member.

* * * * *